(12) United States Patent
Sotgiu

(10) Patent No.: US 10,732,240 B2
(45) Date of Patent: Aug. 4, 2020

(54) MAGNET ASSEMBLY FOR MRI COMPRISING CYLINDRICAL RINGS OF HALBACH TYPE

(71) Applicant: Antonello Sotgiu, Teramo (IT)

(72) Inventor: Antonello Sotgiu, Teramo (IT)

( * ) Notice: Subject to any disclaimer, the term of this patent is extended or adjusted under 35 U.S.C. 154(b) by 113 days.

(21) Appl. No.: 15/767,668

(22) PCT Filed: Oct. 25, 2016

(86) PCT No.: PCT/IT2016/000252
§ 371 (c)(1),
(2) Date: Apr. 12, 2018

(87) PCT Pub. No.: WO2017/072805
PCT Pub. Date: May 4, 2017

(65) Prior Publication Data
US 2018/0313920 A1 Nov. 1, 2018

(30) Foreign Application Priority Data

Oct. 26, 2015 (IT) .................. 102015000065509

(51) Int. Cl.
*G01R 33/383* (2006.01)
*A61B 5/055* (2006.01)
(Continued)

(52) U.S. Cl.
CPC ............ *G01R 33/383* (2013.01); *A61B 5/055* (2013.01); *G01R 33/3873* (2013.01); *H01F 7/0278* (2013.01)

(58) Field of Classification Search
CPC . G01R 33/383; G01R 33/3873; H01F 7/0278; A61B 5/055
See application file for complete search history.

(56) References Cited

U.S. PATENT DOCUMENTS

| 4,703,276 A | 10/1987 | Beer |
| 5,148,138 A | 9/1992 | Miyata |
| (Continued) | | |

FOREIGN PATENT DOCUMENTS

| JP | 63-9102 | 1/1988 |
| JP | 4-144541 | 5/1992 |
| WO | WO 2007/120057 | 10/2007 |

OTHER PUBLICATIONS

International Search Report dated Apr. 19, 2017 issued in PCT International Patent Application No. PCT/IT2016/000252, 4 pp.
(Continued)

*Primary Examiner* — Susan S Lee
(74) *Attorney, Agent, or Firm* — Nixon & Vanderhye P.C.

(57) ABSTRACT

Construction methods and techniques allow for a magnetic field of the field homogeneity required for the use in magnetic resonance imaging (MRI), in the order of 20 parts per million (ppm) in the area of interest (such techniques in the following will be indicated with the word "shimming"). The peculiarity of the constructive method is to obtain a homogeneous field region, usable for the MRI analysis, of linear dimensions equal to about 40% of the linear dimensions of the magnet. The shimming technique involves the use of conditioned magnetic material and allows accurate control of the magnetization of the corrective elements while using a material that inherently has a large spread in the magnetization value. The result is a low weight and small magnet suitable for MRI for dedicated clinical applications such as the analysis of the peripheral joint, the analysis of the ocular region, and veterinary applications.

10 Claims, 5 Drawing Sheets a)

b)

(51) Int. Cl.
*H01F 7/02* (2006.01)
*G01R 33/3873* (2006.01)

(56) References Cited

U.S. PATENT DOCUMENTS

| | | |
|---|---|---|
| 6,191,584 B1 | 2/2001 | Trequattrini et al. |
| 6,680,663 B1 | 1/2004 | Lee et al. |
| 2008/0197845 A1 | 8/2008 | Trequattrini et al. |
| 2009/0128272 A1 | 5/2009 | Hills |
| 2010/0301861 A1 | 12/2010 | Pittaluga et al. |
| 2011/0084695 A1 | 4/2011 | Besio et al. |
| 2013/0176024 A1* | 7/2013 | Pors .................. G01F 1/716 324/306 |
| 2014/0111202 A1 | 4/2014 | Wald et al. |

OTHER PUBLICATIONS

Bjørk, R. et al., "Optimization and Improvement of Halbach Cylinder Design", Journal of Applied Physics, vol. 104, No. 1, Jul. 9, 2008, 10 pp.

Danieli, Ernesto et al., "Mobile Sensor for High Resolution NMR Spectroscopy and Imaging," Journal of Magnetic Resonance, vol. 198, No. 1, May 1, 2009, pp. 80-87.

Jachmann, Rebecca C. et al., "Multipole Shimming of Permanent Magnets Using Harmonic Corrector Rings," Review of Scientific Instruments, vol. 78, No. 3, Mar. 30, 2007, 9 pp.

Phuc, Hung Dang et al., "Design and Construction of Light Weight Portable NMR Halbach Magnet," International Journal on Smart Sensing and Intelligent Systems, vol. 7, No. 4, Dec. 1, 2014, pp. 1555-1578.

Raich, H. et al., "Design and Construction of a Dipolar Halbach Array with a Homogeneous Field from Identical Bar Magnets: NMR Mandhalas," Concepts in Magnetic Resonance, NMR Concepts, vol. 23B, No. 1, Jan. 1, 2004, pp. 16-25.

Soltner, H. et al., "Dipolar Halbach Magnet Stacks Made from Identically Shaped Permanent Magnets for Magnetic Resonance," Concepts in Magnetic Resonance, Part A, vol. 36A (4), 2010, pp. 211-222.

* cited by examiner

Fig. 5
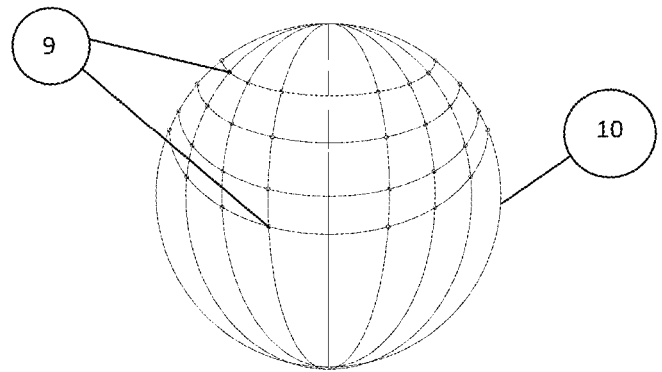
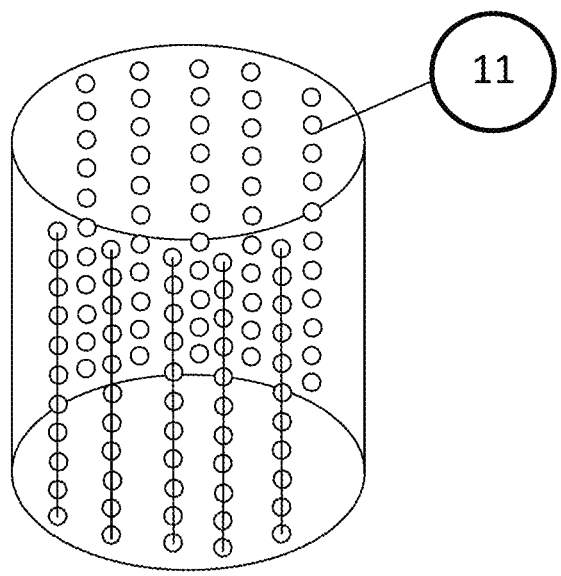
Fig. 6

MAGNET ASSEMBLY FOR MRI COMPRISING CYLINDRICAL RINGS OF HALBACH TYPE

This application is the U.S. national phase of International Application No. PCT/IT2016/000252 filed Oct. 25, 2016 which designated the U.S. and claims priority to Italian Patent Application No. 102015000065509 filed Oct. 26, 2015, the entire contents of each of which are hereby incorporated by reference.

The present invention identifies the construction methods and the techniques that allow to obtain a magnetic field of the field homogeneity required for the use in magnetic resonance imaging (MRI), in the order of 20 parts per million (ppm) in the area of interest (such techniques in the following will be indicated with the word "shimming"). The peculiarity of the described constructive method is to obtain a homogeneous field region, usable for the MRI analysis, of linear dimensions equal to about 40% of the linear dimensions of the magnet. The shimming technique involves the use of conditioned magnetic material and allows to control accurately the magnetization of the corrective elements while using a material that inherently has a large spread in the magnetization value. The result is a low weight and small magnet suitable for MRI for dedicated clinical applications such as the analysis of the peripheral joint, the analysis of the ocular region, veterinary applications.

TECHNICAL FIELD

The invention is in the field of systems and methods for imaging by magnetic resonance. More particularly it relates to systems and methods for dedicated MRI scanner. A dedicated MRI scanner is a device that can perform MRI analysis in a limited part of the human body. The magnets for these applications are smaller than those normally used clinical diagnosis ("whole body" systems) and have smaller uniformity regions. The typical Field of View (FOV) of clinical systems for man is a sphere 40/50 cm in diameter, while the FOV of a dedicated peripheral joint system (hand, foot, knee) is a sphere about 16 cm in diameter. In general, dedicated systems operate at a value of the magnetic field of the order of 0.15 T-0.3 T, and are defined "low field systems".

BACKGROUND ART

The magnet is the most critical part of an MRI scanner and must have very good field homogeneity in a significant fraction of its internal volume. Dedicated scanners are described in patents such U.S. Pat. No. 6,191,584B1, US20080197845A1, US20100301861A1, US2011-0084695A1. Their magnetic structure includes: the magnetic material, the yoke and the magnetic poles. The homogeneity region of the magnet is contained between the poles and the part of the body under examination is inserted in this region. The presence of the yoke and of the iron pole has the following drawbacks:
  Iron introduces magnetic losses, and this requires a greater amount of magnetic material to generate a given magnetic field;
  It greatly increases size and weight of the magnet;
  The shimming procedure becomes more complex and empirical due to the non-linearity of the iron magnetic susceptibility.

A circular Halbach ring is a particular arrangement of permanent magnet blocks (see FIG. 2) which increases the magnetic field along one direction while canceling the orthogonal component of the magnetic field. This is achieved by rotating the direction of magnetization as a function of the azimuthal position of the blocks in the ring. One of the main advantages of a Halbach ring is that it does not require an iron yoke to confine the magnetic field. FIG. 2 shows different implementations: in FIG. 2a the direction of the magnetization changes continuously along the material; FIGS. 2b and 2c show implementations with a discrete number of blocks. In FIG. 2c the variation of the magnetization is obtained by rotating the blocks, on the contrary in FIG. 2b is the block magnetization inside the blocks to be rotated. The case of FIG. 2a implies a magnetic treatment of the entire ring which is technologically impractical particularly for a large magnetic device. The design of FIG. 2b requires that the blocks are magnetized, at the same value of the residual magnetization, along different directions. This is also difficult to obtain since the dimension of the blocks along the magnetization direction is different at different orientations. The main effect, in any case, is that a continuous distribution of the magnetization directions is replaced by a discrete distribution. The discretization has the effect of reducing the field uniformity along the radial direction, this reduction increases when the number of blocks in the ring is reduced. All the drawings of FIG. 2 are two-dimensional and involve an infinite length along the direction perpendicular to the plane. The MRI magnets have, obviously, a finite length and, in addition, the magnet length must be as short as possible to allow placing the part under examination in the center of the FOV. It is then necessary to find a different way to maximize the fraction of the magnet internal volume which has a suitable field homogeneity. In literature there are different designs of Halbach magnets aimed to increase the uniformity of the magnetic field. In particular H. Raich, P. Blumer "Design and Construction of a Dipolar Halbach Array with a Homogeneous Field from Identical Bar Magnets: NMR Mandhalas" Concepts in Magnetic Resonance Part B (Magnetic Resonance Engineering), Vol. 23B (1) 16-25 (2004) presents a 2D simulation using the finite element method of cubic blocks magnetized along an identical axis and placed at different orientations. The resulting magnet is formed by a stack of 8 identical rings and has a region of uniformity of about 20 mm. Bjørk R. et al. "Optimization and improvement of Halbach cylinder design", J. Appl. Phys. 104, 013 910_2008, analyze the behavior of a hypothetical Halbach ring of cylindrical shape and describe the magnetic field shape as a function of the magnet height and of the inner and outer radius. Jachmann R. C. et al. "Multipole shimming of permanent magnets using harmonic corrector rings", Rev. Sci. Instrum. 78, 035 115_2007, finally describe a 2D technique based on the correction of successive harmonics of the development of the field in series of powers. These papers, however, do not help to find a building modality which uses identical blocks, identical magnetization direction in a device with a large fraction of uniform magnetic field. Up to now, in spite of the fact that Halbach rings would represent a convenient way to build the magnets for small dedicated MRI, systems, they are not commonly used. Moreover the need to manufacture permanent magnetic blocks magnetized along different directions requires magnetization methods and equipment which are out of reach of most of magnetic materials producers. The U.S. Pat. Nos. 4,703,276, 5,148,138, 6,680, 663, describe the use of blocks with different orientations of the magnetization direction. The patents US20090128272 and US20140111202 describe a similar principle, in the first the magnetic field is produced by four bars of magnetized material and the homogeneity region is a small fraction of the total volume. The second describes a portable device in which the size of the magnetized bars are very small and the resulting magnetic field is necessarily low. Both models also do not take into account the finite length of the bars causing a further reduction in the homogeneity region. An attempt to account for the finite length of the magnet is presented in patent WO 2007120057 in which the central blocks are placed at a distance calculated in such a way to cancel the second order coefficients of the field development in series power of (see WO 2007120057, claims 18, 21, 22, 23, 24, 25, 26) the result of this choice is that the uniformity of the region has linear dimensions ranging from one third to a tenth of the magnet height (see WO 2007120057 FIG. 3-8). A further element which tends to reduce the homogeneity of the field along the radial direction is that to obtain the required distribution of the magnetization directions using identical blocks they are rotated so as to present different surfaces in the radial direction including the edges of the blocks. This produces a non-uniform distribution of the potential which tends to reduce the homogeneity of the magnetic field inside.

In an exemplary embodiment, apparatus for diagnostic by magnetic resonance is configured to generate a uniform magnetic field in a field of view. The apparatus has a main longitudinal axis and includes two external Halbach ring of magnets positioned symmetrically with respect to a center of the longitudinal axis and a plurality of internal Halbach sets of magnets integrally coupled to a support structure formed by collars and rings, placed in pairs symmetrically with respect to the center of the longitudinal axis. The internal and external arrangements are positioned at different positions along the main longitudinal axis of the apparatus so that the two external arrangements are at the two end positions of the apparatus. The magnets of the external and internal arrangements are identical to each other and have a right prism shape with a N sides regular polygon base, whereby the right prism has a longitudinal axis and N side faces parallel to the longitudinal axis. Each magnet generates a magnetic field directed orthogonally to the center of one of its N side faces, and each of the external and internal arrangements of Halbach ring magnets includes a number P of elements arranged such that their longitudinal axes are positioned on a circumference centered on the main longitudinal axis of the apparatus, each one with an angular position and the longitudinal axes of two adjacent magnets have a mutual angular distance equal to 360°/N, and such that the magnetic fields of two adjacent magnets are oriented in directions forming an angle equal to 720°/N between themselves. The longitudinal axes of the magnets of each external arrangement are positioned on a circumference having a radius $r_{est}$, and the longitudinal axes of the magnets of each internal arrangement are positioned on a circumference having a radius $r_{int}$, where the radius $r_{int}$ is greater than the radius $r_{est}$, wherein the longitudinal axis of each magnet of an internal arrangement is positioned at an angular position α equidistant between the angular positions of the two closest magnets of each of the two arrangements adjacent to that to which belongs the magnet under consideration, whereby the field of view has a shape of a sphere centered at the geometric center of the plurality of the internal arrangements of Halbach ring magnets. At least one of two external arrangements of Halbach ring magnets is provided with an opening configured to allow access to the field of view from outside.

In another exemplary embodiment, a method of homogenization of the magnetic field generated in the field of view by an apparatus for diagnostic by magnetic resonance is configured to generate a uniform magnetic field in a field of view. The apparatus has a main longitudinal axis and includes the two external Halbach rings of magnets of the described embodiments. The method includes the steps of (A) measuring the magnetic field generated by the two external arrangements of Halbach ring magnets and by the plurality of internal arrangements of Halbach ring magnets at a plurality of points of the field of view identified by the intersection of parallel and meridian curves; (B) calculating a magnetization to be applied to each of primary shim element in order to make the magnetic field homogeneous in the field of view; (C) magnetizing each primary shim element in accordance with the calculation of step B; (D) positioning in the apparatus the plurality of primary shim elements magnetized in step C; (E) measuring the magnetic field generated by the two external arrangements of Halbach ring magnets and by the plurality of internal arrangement of Halbach ring magnets, adjusted by the plurality of magnetized primary shim elements, at a plurality of points of the field of view; (F) calculating a magnetization to be applied to each secondary shim element so as to make homogeneous the magnetic field in the field of view; (G) magnetizing each secondary shim element in accordance with the calculation of step F; and (H) positioning the corresponding secondary shim element magnetized in step G in said at least one housing seat of each primary shim element.

DISCLOSURE OF THE INVENTION

The present invention identifies the methods of construction and shimming of a magnet for clinical application built using Halbach rings to obtain a homogeneous field in a region, internal to the magnet, of linear dimensions equal to about 40% of the size of the magnet. The rings are assembled using blocks of identical size, magnetized along a direction perpendicular to one of the side surfaces of the blocks. The whole magnet consists of 6 Halbach rings each composed of 16 identical blocks as shown in FIG. 1a and FIG. 1b. The magnetized blocks have a cylindrical shape in which the base is a regular hexadecagon (or a prism with hexadecagon base) (FIG. 3). The direction of magnetization is perpendicular to the cylinder axis and directed towards the center of one of the 16 lateral faces. The different orientations of the magnetization are obtained, in the construction phase, by rotating the blocks according to the angular position in which they must be placed. A cylindrical inner hole allows to fix the blocks to the supporting structure. In the example of FIG. 1a and FIG. 1b the magnet is composed of six rings of magnetic material each made up of 16 blocks. FIG. 4 shows the longitudinal section of the magnet. To reduce the effect of the finite length of the magnet is possible to act on the different geometrical parameters of FIG. 4 (R1, R2, D0, D1, D2). The optimization can be performed either using analytical tools or numerical techniques. The flux density of each ring, can be written as:

$$B(x) = \frac{\mu}{4*\pi} \sum_{i=1}^{n-1} \frac{3*(m_i*n_i)*n_i - m_i}{(r^2+x^2)^{3/2}}$$

where $m_i$ are the magnetic moments of the individual blocks and $n_i$ are the unit vectors that give the position of the blocks:

$$m_i = m \begin{bmatrix} 0 \\ \sin(\beta_i) \\ \cos(\beta_i) \end{bmatrix}$$

$$n_i = \frac{1}{(r^2 + x^2)^{1/2}} \begin{bmatrix} x \\ r*\sin(\alpha_i) \\ r*\cos(\alpha_i) \end{bmatrix}$$

where $\beta_i$ gives the orientation of the magnetization and $\alpha_i$ its angular position.

Analytical techniques give an accuracy of the order of 5% (H. Soltner, P. Blumer, Concepts in Magnetic Resonance, Part A, Vol 36A (4) 211-222). However modern magnetic field simulation programs coupled to optimization techniques in which it is possible to insert the required constraints have reduced the importance of an analytical approach. Many parameters of the proposed design can be bound in order to obtain a design that meets the constraints required by the magnet applications. The first constraint is the bore of the magnet (OPEN BORE in FIG. 4), which determines the size of the objects that can be inserted, the second is the FOV (7) which usually has the shape of a sphere positioned in the geometrical center of the magnet and defined by its diameter. Also important are the distances: magnet_end/FOV_end and magnet_end/FOV_center (L0, L1).

The way in which different materials are used for the shimming of the magnets is described in many scientific papers and patents. In view of the fact that traditional magnets have iron poles most of the shimming techniques are directed toward the shaping of the poles to optimize the magnetic field homogeneity. However, also in this case, after optimization of the pole surface, the next step is to add iron elements or magnetic material to further improve the homogeneity (these elements will be hereinafter referred to as "shim elements or shims").

The established technique for the final shimming consists in the following operations:
1. The initial magnetic field is measured in a given number of points that define the contours of the desired FOV (see FIG. 5);
2. The magnetic field produced by the shim elements placed in a number of positions that depend on the geometry of the magnet, is determined experimentally or through simulations. In the case of iron shim elements what is measured or determined numerically is the magnetic field variation caused by the insertion of such elements.
3. Through mathematical techniques of linear programming the number of magnetic elements of given dimensions to be placed on each pole to obtain a homogeneous field is determined.

The solution obtained from this technique is a set of numbers, presumably not integers, representing the number of elementary shim elements that should be placed in the selected positions. In view of the fact that the shimming elements can be realized in a limited number of dimensions this number can only be approximated by real shimming elements and the correction will be only approximate. Because of this, several authors have proposed approximation techniques based on the use of integer numbers, which use, for the shim magnets a limited number of sizes. In this case the result will actually be an integer that represents the number (or numbers) of elementary magnets that must be placed in different positions to correct the magnetic field. These techniques may give a precise solution, but it would require an accurate knowledge of the residual magnetization of the shim elements which is known with an accuracy of the order of 4-6%. This involves a serious problem when the required homogeneity is in the order of 10-20 ppm and the amount of shimming material is a non negligible fraction of the total magnetic material ($^1\!/_{100}$ by mass). The shimming elements in this case have an intrinsic error higher of the required accuracy of the magnetic field. This requires to make subsequent cycles shimming using progressively smaller correction elements.

Figure 1:
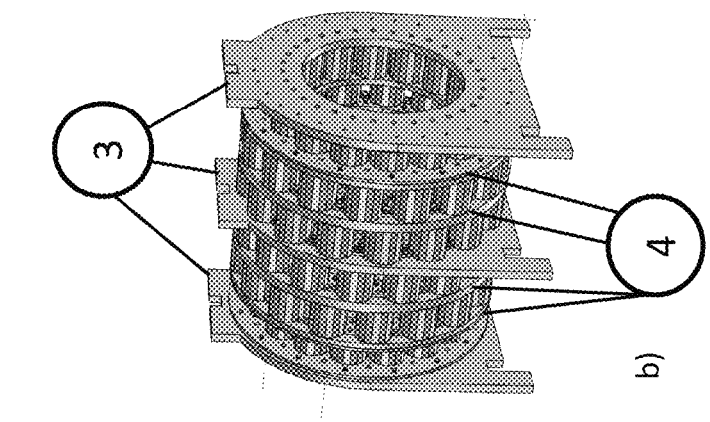
FIG. 1
Figure 1:
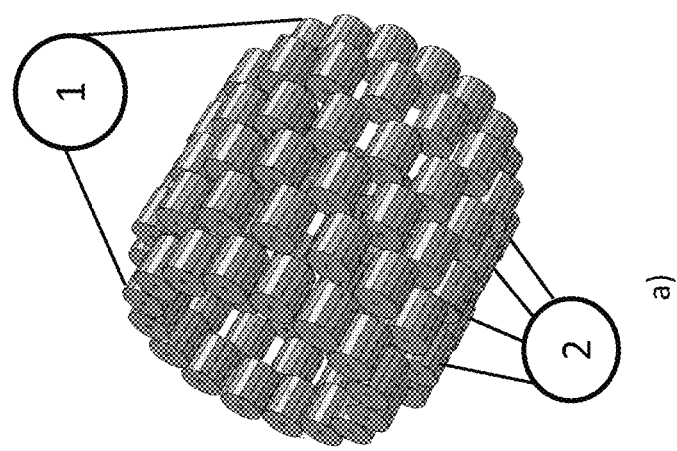
Figure 2:
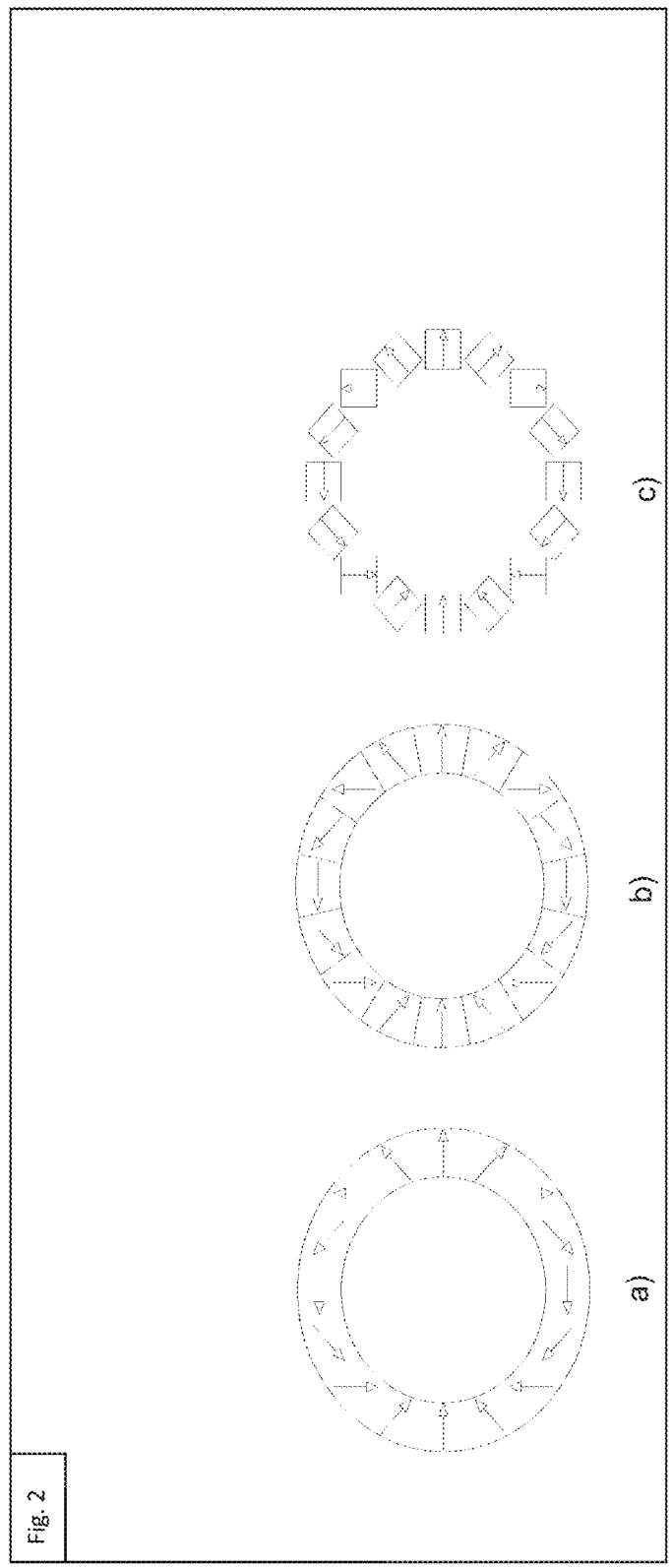
Figure 3:
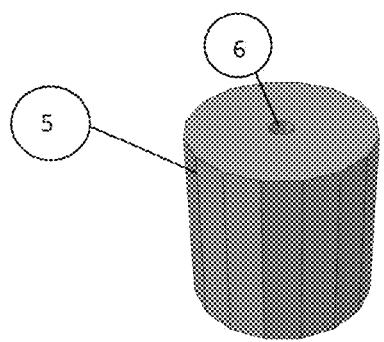

A) Position of the magnetic blocks in the construction of the magnet. The rings are rotated to allow the insertion of fastening elements. Two types of Halbach rings of different radii are present: the outer rings (1) and inner rings (2). B) General structure of the fastening elements. The Halbach rings are held rigidly in position by holding structures such as collars (3) connected among them by longitudinal bars not shown in the figure and by circular rings (4). All these elements are made of aluminum.

FIG. 2

Possible implementation of Halbach rings. A) Continuous variation of the magnetization direction within a homogeneous ring. B) Assembly of a ring by geometrically identical elements with rotated direction of the magnetization. C) Ring made of identical blocks and magnetized along the same direction. The Halbach ring distribution of is obtained by rotation of the entire blocks.

FIG. 3

Cylindrical block with hexadecagonal base (or prism with hexadecagonal base). The central hole (6) allows fixing the block to the aluminum structure. The magnetization is directed perpendicularly to one of the 16 side faces (5).

FIG. 4

Longitudinal section of the magnet. The terminal rings (outer or external rings), indicated with 1 in figure, have a smaller radius than the central rings (inner or internal rings) indicated with 2. The blocks are rigidly fixed to the internal supporting elements (4) and to the central and lateral supports (3). The FOV (7) has a diameter of up to 18 cm. L0 and L1 respectively represent the distances: magnet_end/FOV_end and magnet_end/FOV_center. D0, D1 and D2 are the thicknesses of the support elements which determine the longitudinal position of the rings.

FIG. 5

For the purposes of shimming the magnetic field is measured both on the surface of the FOV and on an inner spherical surface. The measurement points are placed at the intersection of parallel lines (9) and meridian lines (10) of spheres of radius FOV/2 and FOV/4.

FIG. 6

Position (11) of the shim elements in the case of a Halbach magnet. The elements are placed with the magnetization aligned to the direction of the magnetic field.

FIG. 7

The shim rings (12) are placed on aluminum longitudinal bars (14) connected firmly to the support structure of the magnet. Secondary shims (13) are placed inside the primary shimming elements (12).

FIG. 8

The shim elements can have different geometrical shapes such as circular (12) or square (15). In both cases the secondary shims are placed inside the primary shim elements.

DETAILED DESCRIPTION OF THE PREFERRED EMBODIMENT: MAGNET CONSTRUCTION

The magnet, whose preferred embodiment is shown in FIG. 1, is formed by 6 Halbach rings divided into two subgroups, the inner rings (2) and the two outer rings (1). Each ring has 16 blocks of cylindrical shape with hexadecagonal base (FIG. 1). The magnetization of the blocks is perpendicular to the cylinder axis and directed towards the center of one of the faces. The orientation of the magnetization of the rings is such as to perform a rotation of 720° within one revolution. A magnet located in the angular position $\alpha$ will therefore have an orientation of magnetization equal to $2*\alpha$.

Figure 4:
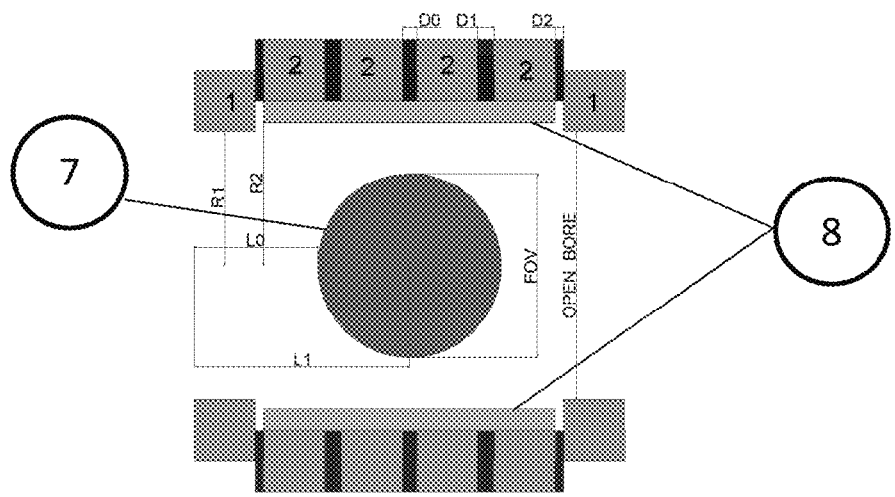

As shown in FIG. 4 the inner rings have the same radius while the end rings are placed at a smaller radius so as to partially compensate for the effect of the finite length of the magnet. The supports that hold the magnet are aluminum. The rotation of the magnetization on each ring confines the magnetic field within the magnet and does not need an iron structure nor as a yoke or in the form of pole. This, at parity of dimensions and of magnetic material, allows to obtain the maximum value of the magnetic field.

The material used for shimming the magnetic field to obtain the required homogeneity of the magnet is placed in the inner zone in close thermal contact with the main blocks and with the metallic support structure. This avoids thermal fluctuations between the different components of the magnet and allows to stabilize the magnet as a unique structure to a same temperature. For the same reason the entire magnet is shielded both internally and externally by a layer of thermally insulating material (not shown in the figure). In the demonstration prototype of the preferred embodiment the distance L0 between the outside of the magnet and the homogeneity of the region is equal to 13 cm and the diameter of the FOV (7) is equal to 18 cm. The total length of the magnet is 45 cm. It can be utilized for the study of peripheral joints (hands, feet, knees etc. . . . ), for ophthalmology applications being it possible to study the ocular region without entering the patient's shoulders inside the magnet and for the study of small pets up to a mass of 18-20 kg.

DETAILED DESCRIPTION OF THE PREFERRED EMBODIMENT: SHIMMING

The shimming procedure that has been developed consists in the following cycle:

A. The magnetic field is measured in a series of points that identify the physical region in which the field homogeneity is requested. This operation can be done via field meters that use NMR probes and that have an accuracy of $1/10^8$ or via Hall probes. Currently calibrated Hall probes have an accuracy of $1/10^6$ and are therefore suitable for this application. A further advantage is that while the measuring head of the NMR probe has linear dimensions of the order of 0.6 cm, the sensors used in the Hall probes have linear dimensions of the order of a fraction of millimeter. The determination of the probe position is therefore more accurate. The head of the Hall sensor measurement is brought into position, under computer control and with micrometric precision, by a motorized XYZ positioner. The number of points on which the magnetic field is measured is critical and their number needs to be evaluated experimentally. In the specific case the points on the spherical surface which delimits the FOV are equidistant along 16 parallel (9) and 16 meridians (10) on two concentric spheres of a radius equal to the radius of the FOV and half of this. At these values it is added to the value of the field at the center of the FOV for a total of 513 points.

Figure 7:
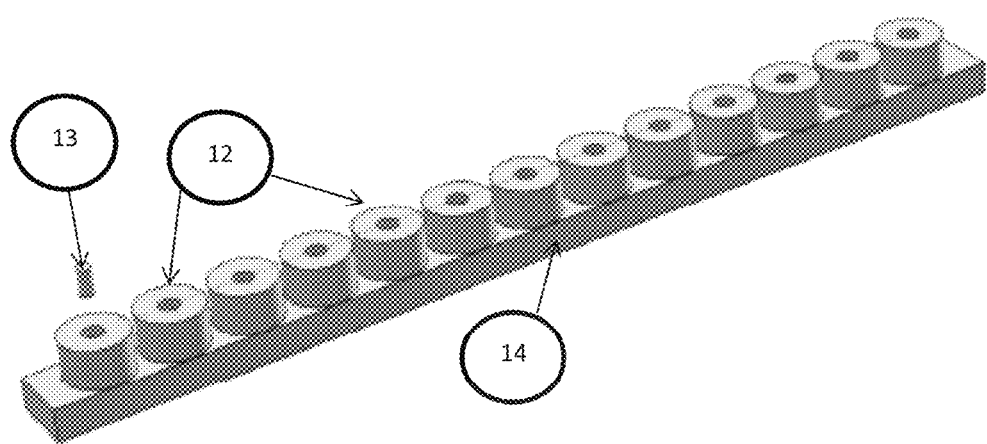
Figure 8:
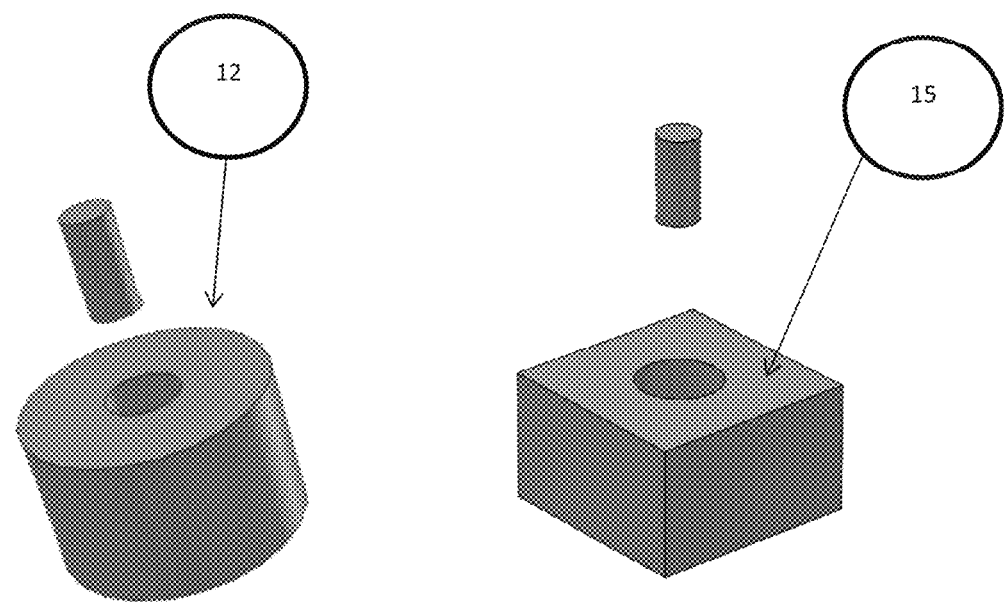

B. To determine the effect of the insertion of the individual shims on the previously selected 513 points the shim elements should be placed in position (see FIG. 6) and their effect measured in each of the target points. For an high number of target points and shims this would be too long and virtually impossible. This step is then replaced by the determination of the effect of the shims using magnetic field simulation programs. Thus in this step a simulation program evaluates the changes in the magnetic field generated by each of the primary shim (cylindrical rings or parallelepipeds) in each of the spatial positions in which the shim elements will be placed. The shim elements taken into account are cylindrical (12) or rectangular with a central hole. In both cases, the central holes are used to insert a second element of shims (shim secondary) (13) as shown in FIG. 7.

C. At this points through linear programming techniques a vector M (i) that provides the magnetization values which must be applied to the i-th primary shim to obtain an homogeneous magnetic field, is calculated. This is done easily using specific functions present in the mathematical calculation CADs (Mathematica, MATLAB, MATCAD etc. . . . ) of the kind "Linear-Programming".

D. The required value of the magnetization is applied to each element by means of a specific apparatus magnetizer/conditioner that will bring the magnetization to the required value. This procedure is repeated for all the primary shims. Since the apparatus used to condition the magnetization has an accuracy of about 1% the obtained magnetizations will be slightly different from the required values.

E. At this point the shims are placed in position and the magnetic field produced by the magnet and by the primary shim elements is measured in all the 513 target points;

F. Using again simulation programs, the variation introduced by the secondary shims (13) inserted inside of the primary shim (12) (15) is determined;

G. Through linear optimization techniques the values of the magnetization for the individual secondary shim is calculated;

H. The procedure from point D is repeated on the secondary shims; also this time the accuracy that can be reached is of the order of one percent. However, since it has to do with much smaller elements, the cumulative effect of these two operation corresponds to have an accuracy on shim elements between 0.1% to 0.01% which is much better it is possible to obtain with different technique of magnetization conditioning.

I. At this point the elements of secondary shims are positioned within the primary ones.

In this way it is possible to obtain a field uniformity equal to about 20 ppm in a region of linear dimensions equal to 40% of the height of the magnet. This result is essentially better of those obtained in other types of magnet with traditional shim techniques.

The invention claimed is:

1. Apparatus for diagnostic by magnetic resonance configured to generate a uniform magnetic field in a field of view, wherein the apparatus has a main longitudinal axis and comprises two external Halbach ring of magnets positioned symmetrically with respect to a center of the longitudinal axis and a plurality of internal Halbach sets of magnets integrally coupled to a support structure formed by collars and rings, placed in pairs symmetrically with respect to the center of the longitudinal axis, the internal and external arrangements being positioned at different positions along the main longitudinal axis of the apparatus so that the two external arrangements are at the two end positions of the apparatus, the magnets of the external and internal arrangements being identical to each other and having a right prism shape with a N sides regular polygon base, whereby the right prism has a longitudinal axis and N side faces parallel to said longitudinal axis, wherein each magnet generates a magnetic field directed orthogonally to the center of one of its N side faces, each of the external and internal arrangements of Halbach ring magnets comprises a number P of elements arranged such that their longitudinal axes are positioned on a circumference centered on the main longitudinal axis of the apparatus each one with an angular position $\alpha_i$ and the longitudinal axes of two adjacent magnets have a mutual angular distance equal to 360°/N, and such that the magnetic fields of two adjacent magnets are oriented in directions forming an angle equal to 720°/N between themselves, wherein the longitudinal axes of the magnets of each external arrangement are positioned on a circumference having a radius $r_{est}$ and the longitudinal axes of the magnets of each internal arrangement are positioned on a circumference having a radius $r_{int}$, where the radius $r_{int}$ is greater than the radius $r_{est}$, wherein the longitudinal axis of each magnet of an internal arrangement is positioned at an angular position $\alpha$ equidistant between the angular positions of the two closest magnets of each of the two arrangements adjacent to that to which belongs the magnet under consideration, whereby the field of view has a shape of a sphere centered at the geometric center of the plurality of the internal arrangements of Halbach ring magnets, at least one of two external arrangements of Halbach ring magnets being provided with an opening configured to allow access to the field of view from outside.

2. Apparatus according to claim 1, wherein the number N of side faces of each magnet is equal to the number of magnets of each external and internal arrangements, such that the magnetization of each block is always directed perpendicular to one of the N side faces of the blocks.

3. Apparatus according to claim 1, wherein the number of internal arrangements of Halbach ring magnets is an even number, i.e. 2·I, where I indicates an integer, wherein the number of Halbach ring internal and external arrangements is optionally equal to 6.

4. Apparatus according to claim 1, wherein the support structure is made of aluminum.

5. Apparatus according to claim 1, wherein the two external arrangements of Halbach ring magnets, the plurality of internal arrangements of Halbach ring magnets, and the support structure are thermally shielded by at least one layer of thermally insulating material.

6. Apparatus according to claim 1, further comprising a plurality of primary shim elements, configured to be magnetized, integrally coupled to the support structure in correspondence with an inner zone of the plurality of internal arrangements of Halbach ring magnets, wherein the inner zone is directed towards the field of view, each primary shim element being provided with at least one housing seat configured to house a corresponding secondary shim element configured to be magnetized, wherein each primary shim element optionally has a cylindrical shape or a parallelepiped shape and comprises a housing seat consisting of a central hole configured to house a corresponding secondary shim element having a cylindrical shape.

7. Method of homogenization of the magnetic field generated in a field of view by an apparatus for diagnostic by magnetic resonance configured to generate a uniform magnetic field in a field of view, wherein the apparatus has a main longitudinal axis and comprises two external Halbach rings of magnets positioned symmetrically with respect to a center of the longitudinal axis and a plurality of internal Halbach sets of magnets integrally coupled to a support structure formed by collars and rings, placed in pairs symmetrically with respect to the center of the longitudinal axis, the internal and external arrangements being positioned at different positions along the main longitudinal axis of the apparatus so that the two external arrangements are at the two end positions of the apparatus, the magnets of the external and internal arrangements being identical to each other and having a right prism shape with a N sides regular polygon base, whereby the right prism has a longitudinal axis and N side faces parallel to said longitudinal axis, wherein each magnet generates a magnetic field directed orthogonally to the center of one of its N side faces, each of the external and internal arrangements of Halbach ring magnets comprises a number P of elements arranged such that their longitudinal axes are positioned on a circumference centered on the main longitudinal axis of the apparatus each one with an angular position $\alpha_i$ and the longitudinal axes of two adjacent magnets have a mutual angular distance equal to 360°/N, and such that the magnetic fields of two adjacent magnets are oriented in directions forming an angle equal to 7209N between themselves, wherein the longitudinal axes of the magnets of each external arrangement are positioned on a circumference having a radius rest and the longitudinal axes of the magnets of each internal arrangement are positioned on a circumference having a radius $r_{int}$, where the radius $r_{int}$ is greater than the radius $r_{est}$, wherein the longitudinal axis of each magnet of an internal arrangement is positioned at an angular position $\alpha$ equidistant between the angular positions of the two closest magnets of each of the two arrangements adjacent to that to which belongs the magnet under consideration, whereby the field of view has a shape of a sphere centered at the geometric center of the plurality of the internal arrangements of Halbach ring magnets, at least one of two external arrangements of Halbach ring magnets being provided with an opening configured to allow access to the field of view from outside, the apparatus further comprising a plurality of primary shim elements, configured to be magnetized, integrally coupled to the support structure in correspondence with an inner zone of the plurality of internal arrangements of Halbach ring magnets, wherein the inner zone is directed towards the field of view, each primary shim element being provided with at least one housing seat configured to house a corresponding secondary shim element configured to be magnetized, wherein each primary shim element optionally has a cylindrical shape or a parallelepiped shape and comprises a housing seat consisting of a central hole configured to house a corresponding secondary shim element having a cylindrical shape, the method comprising the following steps:

A) measuring the magnetic field generated by the two external arrangements of Halbach ring magnets and by the plurality of internal arrangements of Halbach ring magnets at a plurality of points of the field of view identified by the intersection of parallel and meridian curves;
B) calculating a magnetization to be applied to each of primary shim element in order to make the magnetic field homogeneous in the field of view;
C) magnetizing each primary shim element in accordance with the calculation of step B;
D) positioning in the apparatus the plurality of primary shim elements magnetized in step C;
E) measuring the magnetic field generated by the two external arrangements of Halbach ring magnets and by the plurality of internal arrangement of Halbach ring magnets, adjusted by the plurality of magnetized primary shim elements, at a plurality of points of the field of view;
F) calculating a magnetization to be applied to each secondary shim element so as to make homogeneous the magnetic field in the field of view;
G) magnetizing each secondary shim element in accordance with the calculation of step F;
H) positioning the corresponding secondary shim element magnetized in step G in said at least one housing seat of each primary shim element.

8. Method according to claim 7, wherein the field of view is spherical and said plurality of points of the field of view at which the magnetic field is measured in steps A and E comprises equally spaced points on a first spherical surface with radius equal to the radius of the field of view, equally spaced points on a second spherical surface with radius equal to half the radius of the field of view and a center of the field of view.

9. Method according to claim 8, wherein the equidistant points on the first spherical surface with radius equal to the radius of the field of view and on the second spherical surface with radius equal to half the radius of the field of view are positioned along 16 parallels and 16 meridians.

10. Method according to claim 7, wherein the steps A and E are implemented by probes selected among NMR probes and Hall probes, optionally positioned with micrometric precision by means of a motorized positioner.

* * * * *